United States Patent [19]

Kauffman

[11] Patent Number: 4,622,962
[45] Date of Patent: Nov. 18, 1986

[54] PENILE SUPPORT

[76] Inventor: Robert D. Kauffman, 13 Horseshoe Dr., Annville, Pa. 17003

[21] Appl. No.: 724,759

[22] Filed: Apr. 18, 1985

[51] Int. Cl.$^4$ .............................................. A61F 5/40
[52] U.S. Cl. .................................... 128/158; 128/160
[58] Field of Search ............... 128/79, 168, 138 R, 128/98, 157, 158, 159, 160, 161, 162

[56] References Cited

U.S. PATENT DOCUMENTS

| 265,672 | 10/1882 | Hart | 128/158 |
|---|---|---|---|
| 375,846 | 1/1888 | Ware | 128/158 |
| 496,747 | 5/1893 | Polock | 128/161 |
| 827,207 | 7/1906 | Boehm | 128/158 |
| 850,298 | 4/1907 | De Mars | 128/158 |
| 1,052,765 | 2/1913 | Strauss | 128/159 |
| 1,477,187 | 12/1923 | Rayne | 128/161 |
| 3,550,590 | 12/1970 | Keilman | 128/161 |
| 3,648,700 | 3/1972 | Warner | 128/79 |
| 3,920,008 | 11/1975 | Lehman | 128/96 |
| 3,931,816 | 1/1976 | Waldmann | 128/78 |
| 4,022,196 | 5/1977 | Clinton | 128/79 |
| 4,378,010 | 4/1983 | McDonald | 128/168 |
| 4,526,167 | 7/1985 | Ebenal et al. | 128/79 |

FOREIGN PATENT DOCUMENTS

| 218923 | 2/1910 | Fed. Rep. of Germany | 128/161 |
|---|---|---|---|
| 260938 | 1/1912 | Fed. Rep. of Germany | 128/79 |
| 613611 | 11/1926 | France | 128/158 |
| 25173 | 8/1908 | Sweden | 128/158 |
| 17155 | of 1907 | United Kingdom | 128/158 |

Primary Examiner—Robert P. Swiatek
Assistant Examiner—Cary E. Stone
Attorney, Agent, or Firm—Thomas Hooker

[57] ABSTRACT

A penile support for holding and isolating the penis from the rest of the body during medical treatment or a post-operative recovery.

4 Claims, 3 Drawing Figures

PENILE SUPPORT

The invention relates to an improved penile support useful to hold the penis comfortably in a desired location adjacent to but physically separated from the remainder of the body. The support is preferably used during medical treatment of the penis and recovery from surgical procedures.

Prior penile supports teach surrounding the organ by a downwardly extending protective sac or bag. See U.S. Pat. Nos. 850,298 and 3,550,590. U.S. Pat. No. 4,378,010 teaches confining the organ in an upright position by the use of straps which are fastened over the organ.

This invention is an improvement over prior art penile supports by providing comfortable, located and isolated confinement of the penis during a recuperative or treatment period in an upright position suitable for catheterization of the urinary tract using a Foley catheter. The support may be used to hold the penis following surgery, typically surgery involved in implanting a prothesis, or during treatment of burns or dermatological problems.

The support is constructed of elastic materials and includes adjustment means permitting its use on different sized patients with different sized organs. A casing surrounds the penis and is secured to the support waistband by snap fasteners to hold the organ in the upright position. Disengagement of the snap fasteners permits the organ to be lowered as required, particularly for urination, and then refixed in the controlled upright recuperative position. The support is less bulky than conventional drapes or bandages, thereby permitting the patient to wear a simple, loose fitting shirt or gown during recuperation.

Other objects and features of the invention will become apparent as the description proceeds, especially when taken in conjunction with the accompanying drawings illustrating the invention, of which there are two sheets and one embodiment.

IN THE DRAWINGS

Figure 1:
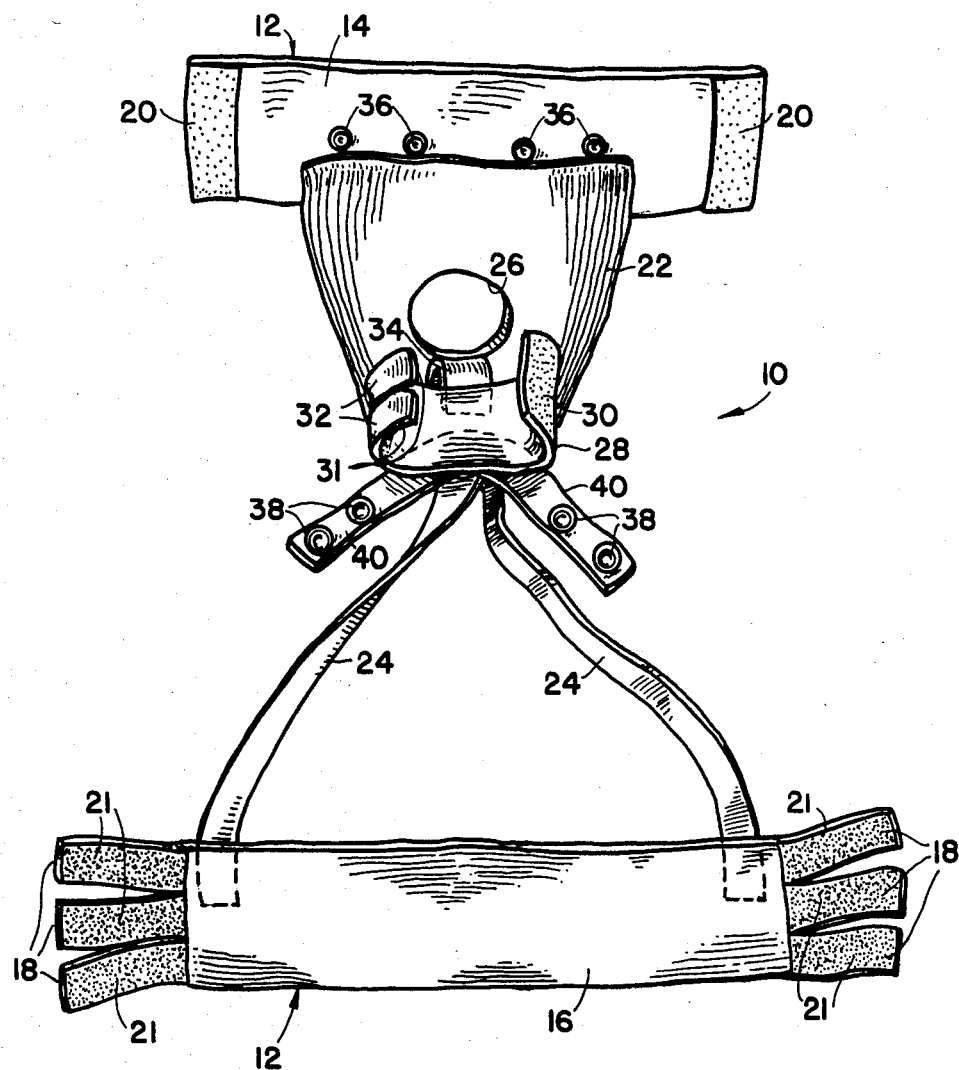
FIG. 1 is a perspective view of the support.
Figure 3:
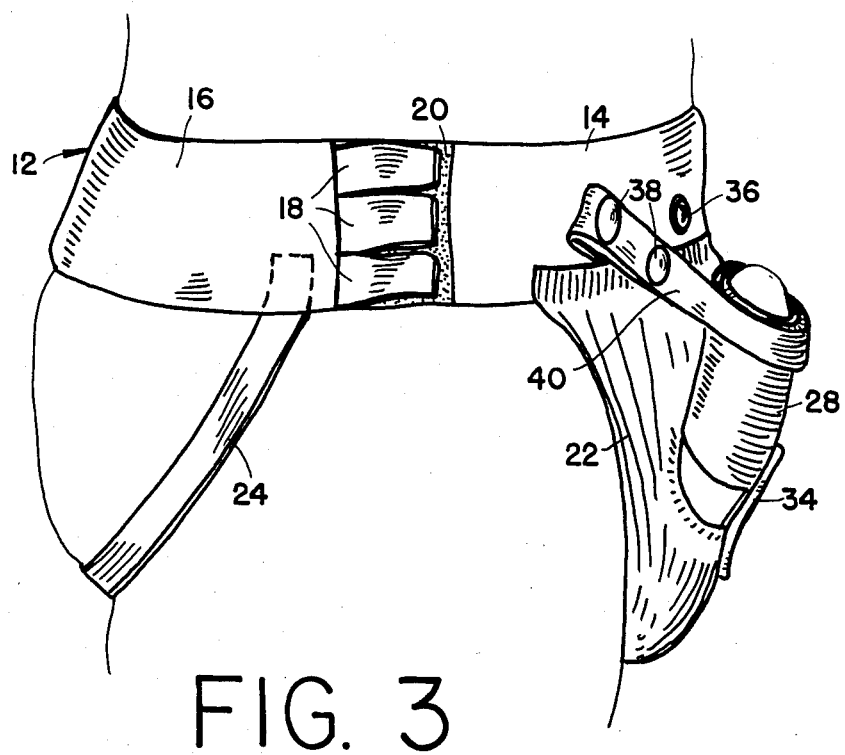

Referring to FIG. 1, penile support 10 includes an elastic waistband 12 formed of front and back elastic waistband members 14 and 16 with suitable Velcro fasteners 20 attached to the ends of member 14 for adjustable engagement with Velcro fasteners 21 secured to the ends of the waistband member 14. Three strips 18 are provided each end of the member 16 to assure that the waistband 12 properly conforms closely and comfortably to the body of the wearer. The Velcro fasteners 20 are secured to the outside surface of front member 14 and fasteners 21 are secured to the inner surface of strips 18, as illustrated in FIG. 1, for engagement with the fasteners 20 as shown in FIG. 3.

Elastic netting scrotum pouch 22 is sewn to the front waistband member 14 and extends downwardly therefrom. The bottom of the pouch is attached to the rear waistband member 16 by a pair of hip straps 24.

A circular opening 26 is formed in the center of pouch 22. Penile casing 28 comprises a length of elastic material which when open extends generally transversely of the pouch. The casing is provided with a Velcro fastener 30 on the outer surface of one end and fastener 31 on the inner surfaces of two strips 32 at the other end of the casing. The Velcro fasteners 30 and 31 permit the casing to be adjustably closed around the penis to support the same during medical treatment or recuperation from an operative procedure, such as placement of a penile implant.

Velcro fasteners 21 and 31 are provided on the inner surfaces of strips 18 and 32 respectively so that these strips are applied to complimentary Velcro fasteners 20 and 30 which face outwardly of the body, thereby permitting the individual smaller strips 18 and 32 to be adjusted one at a time to assure that the waistband is properly and comfortably fitted to the torso of the user and the casing 28 is likewise properly and comfortably fitted to the injured and often painful penis.

Casing 28 is secured to pouch 22 by an elastic hinge strip 34 sewn to the front of the pouch below opening 26 and sewn to the outer surface of casing 28 approximately midway between the ends of the casing. The hinge is secured to the outer surfaces of the pouch and casing to prevent chafing with genitalia when the support is in use.

A row of male snap eyelets 36 is provided along the length of the front waistband member 14 above pouch 22. These eyelets are engagable with the female snap eyelets 38 secured along the lengths of casing adjustment straps 40 extending outwardly at angles from the side of casing 28 away from the hinge strap 34. Straps 40 may be the ends of a single strap sewn to the outer surface of the casing 28 on the side opposite from hinge strip 34 to prevent chafing.

Figure 2:
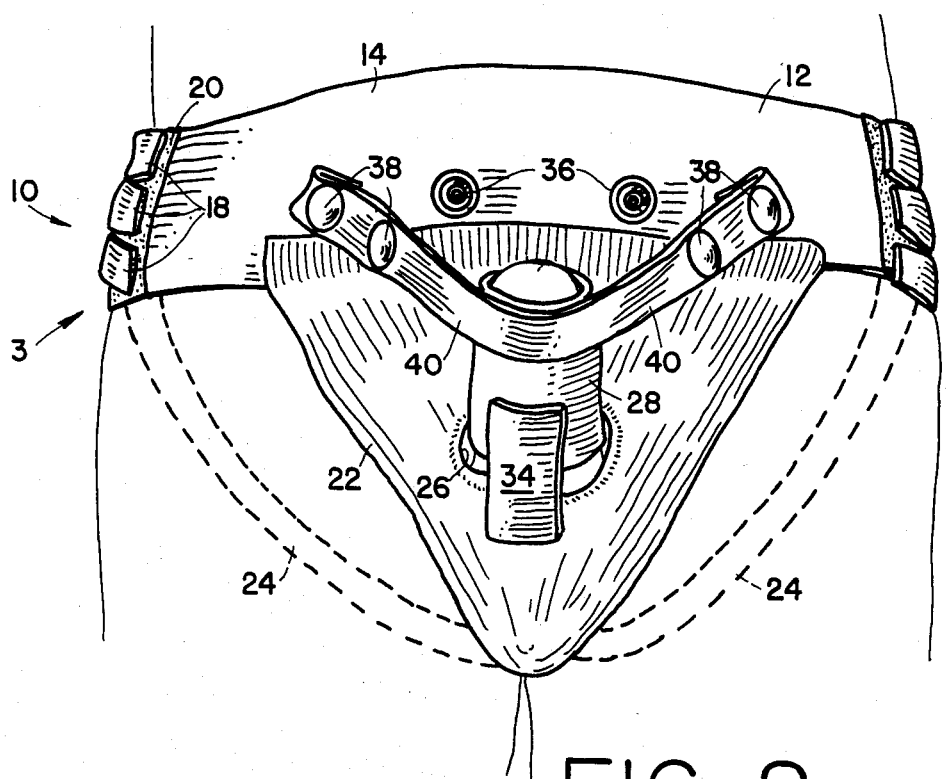
FIGS. 2 and 3 are front and side views respectively of the support in use.

FIGS. 2 and 3 illustrate support 10 in use. The support is worn by the patient by first extending the injured penis through opening 26 so that the pouch 22 surrounds the scrotum, the front waistband member overlies the waist of the patient and hips straps 24 extend rearwardly through the crotch area. The back waistband member 16 is then brought up against the back of the patient as illustrated and the two waistband members are made snug around the waist and strips 18 pressed against the ends of the front member 14 to engage the fasteners 20 and form a continuous waistband 12 which comfortably surrounds the patient and holds the pouch 22 in proper location.

Casing 28 is then closed around the penis which may or may not be bandaged depending upon the requirements of the individual patient. The casing may be closed snugly or loosely as required, following which the Velcro strips 32 are pressed against the opposite end of the casing to engage the fasteners 30 and 31 thereby hold the casing closed in a generally cylindrical configuration for appropriate support of the organ. When surrounded in this manner, the penis may be supported in the upward position as illustrated by snapping the eyelets 38 on the ends of support straps 40 on eyelets 36 on the front waistband member 14, as illustrated. A plurality of eyelets are provided on both the front waistband and on the strips to permit adjusting the upright position of the penis and accommodate different medical support requirements and variations in size of organs. When supported in this manner, the penis is maintained apart from the scrotum and adjacent body of the patient in a fixed, relatively comfortable position where it is protected from undesired and potentially painful contact and movement. Straps 40 hold the penis in the upright position required for retaining a Foley catheter in place for draining the urinary tract.

The straps 40 are readily disengagable from the waistband 12 to permit the penis to be lowered for urination or to permit the casing 28 to be removed from the organ for rebandaging or medical examination.

While the waistband, pouch, casing, hinge strip and hip strips have been described as formed from elastic material, obviously these members may be formed from appropriate cloth or other materials of suitable flexibility and strength as desired.

While I have illustrated and described a preferred embodiment of my invention, it is understood that this is capable of modification, and I therefore do not wish to be limited to the precise details set forth, but desire to avail myself of such changes and alterations as fall within the purview of the following claims.

I claim:

1. A penile support comprising a waistband, a scrotum pouch extending downwardly from the front of the waistband, hip straps joining the bottom of the pouch to the back of the waistband, an opening extending through the center of the pouch, a penile casing extending across the pouch when open, a plurality of adjustable, releasable and resealable overlapping fastening means located along the ends of the casing when the casing is closed, each fastening means including a pair of complementary interengagable surfaces with one surface on the outside of one end of the casing and the other surface on the inside of the other end of the casing whereby the casing may be adjustably closed around a penis extending outwardly through the opening, a single connection between the casing and the pouch consisting of a hinge strip permanently joined to one side of the casing and permanently joined to the pouch below the opening, two casing support straps joining the outside of the opposite side of the casing across from the hinge strap and removable attachment means for securing the ends of the casing support straps to spaced locations on opposite sides of the front of the waistband to hold the casing and surrounded penis in an upward position.

2. A support as in claim 1 including additional removable attachment means for securing the ends of the casing support straps to other spaced locations on the front of the waistband whereby the upward position of the casing may be adjusted.

3. A support as in claim 1 wherein the adjustable fastening means comprises interengagable surfaces on the outer surface of one end of the casing and on the inner surface of the other end of the casing, and wherein the other end of the casing comprises a plurality of strips having a width less than the width of the casing.

4. A support as in claim 3 wherein total width of said strips is essentially equal to the width of the casing to form an essentially continuous fastening along the width of the casing when closed.

* * * * *